United States Patent [19]
Kawabata et al.

[11] Patent Number: 5,466,678
[45] Date of Patent: Nov. 14, 1995

[54] CO-ADMINISTRATION OF S-ADENOSYL-L-METHIONINE TO REDUCE THE NEPHROTOXICITY OF CISPLATIN THERAPY

[75] Inventors: Hironori Kawabata; Koei Moriguchi; Takeshi Endo, all of Nakaniikawa, Japan

[73] Assignee: Fuji Kagaku Kogyo Kabushiki Kaisha, Toyama, Japan

[21] Appl. No.: 211,544

[22] PCT Filed: Sep. 3, 1993

[86] PCT No.: PCT/JP93/01250

§ 371 Date: Apr. 7, 1994

§ 102(e) Date: Apr. 7, 1994

[87] PCT Pub. No.: WO94/05299

PCT Pub. Date: Mar. 17, 1994

[30] Foreign Application Priority Data

Sep. 4, 1992 [JP] Japan .................................. 4-263243

[51] Int. Cl.$^6$ ................................................. A61K 31/70
[52] U.S. Cl. ...................... 514/46; 536/27.31; 424/649
[58] Field of Search ................ 536/27.31; 514/46; 424/649

[56] References Cited

U.S. PATENT DOCUMENTS

| | | | |
|---|---|---|---|
| 2,696,353 | 1/1961 | Shunk et al. | 536/27.31 |
| 3,642,772 | 2/1972 | Haid et al. | 536/26 |
| 3,973,608 | 8/1976 | Umezawa et al. | 435/125 |
| 4,134,918 | 1/1979 | Bey et al. | 564/340 |
| 4,242,505 | 12/1980 | Kawahara | 514/46 |
| 4,369,177 | 1/1983 | Kozaki et al. | 514/46 |
| 4,536,386 | 8/1985 | Keenan | 424/10 |
| 4,670,262 | 6/1987 | Battelli et al. | 424/649 |
| 4,950,465 | 8/1990 | Sato et al. | 424/10 |
| 5,049,396 | 9/1991 | Oftebro et al. | 424/649 |
| 5,114,931 | 5/1992 | Gennari | 514/46 |
| 5,128,249 | 7/1992 | Gennari | 435/113 |
| 5,130,145 | 7/1992 | Oftebro et al. | 424/649 |
| 5,290,538 | 3/1994 | Bertermann | 424/10 |

FOREIGN PATENT DOCUMENTS

| | | | |
|---|---|---|---|
| 0143478 | 6/1985 | European Pat. Off. | 424/649 |
| 3403324A1 | 4/1985 | Germany | 514/46 |
| 3414491 | 10/1985 | Germany. | |
| 56-10920 | 3/1981 | Japan | 536/27.31 |
| 59-139320 | 8/1984 | Japan | 514/46 |
| 61-263925 | 11/1986 | Japan | 424/649 |
| 2-7293 | 2/1990 | Japan | 514/46 |
| 1585203 | 9/1981 | United Kingdom | 424/649 |

OTHER PUBLICATIONS

Tisdale; "Potentiation of the Growth Inhibitory Effects of Adenosine 3', 5'-Monophosphate Analogues by Homocysteine"; Biochemical Pharmacology; vol. 31, No. 6, 1982; pp. 979–982.

Fuchshofen–Rockel et al.; "Prufung Zur Nephrotoxiazitat Von S–Adenosylmethionin (Same) Bei Der Funfesechstelnephrektomierten Ratte"; Verh. Dtsch. Ges. Inn. Med. (Germany, West), vol. BD. 87; 1981; pp. 650–652.

Zager et al., "Acute Amino Acid Nephrotoxicity," *J. Lab. Clin. Med.*, 101(1), 130–140 (1983); *Chem. Abstr.*, 98(11), p. 445, Abstr. No. 88032u (1983); only Abstract supplied.

*Primary Examiner*—Douglas W. Robinson
*Assistant Examiner*—L. Eric Crane
*Attorney, Agent, or Firm*—Nixon & Vanderhye

[57] ABSTRACT

A pharmaceutical composition for use as a nephrotoxicity alleviator for alleviating the nephrotoxicity caused by a drug administered into the living organism, which composition contains S-adenosyl-L-methionine or a salt thereof as an active ingredient is provided. Also provided is a pharmaceutical composition for use as an agent for potentiating the antitumor activity of platinum complex compounds, which composition contains S-adenosyl-L-methionine as an active ingredient.

6 Claims, No Drawings

CO-ADMINISTRATION OF S-ADENOSYL-L-METHIONINE TO REDUCE THE NEPHROTOXICITY OF CISPLATIN THERAPY

Field of Industrial Application

The present invention relates to a pharmaceutical composition containing S-adenosyl-L-methionine or a salt thereof as an active ingredient. More particularly, this invention relates to a pharmaceutical composition for use as a nephrotoxicity alleviator capable of alleviating the nephrotoxicity caused by a drug administered to the living organism, which composition contains S-adenosyl-L-methionine or a salt thereof (hereinafter referred to as SAMes), and also to a pharmaceutical composition for use as an antitumor activity potentiator capable of potentiating the antitumor activity of a platinum complex compound, which composition contains SAMes as an active ingredient.

Background Art

A variety of drugs have currently been in use for the treatment of different malignant tumors. Cisplatin (cis-diamine-dichloroplatinum: CDDP), above all, is an excellent drug with which an increase in life span can be expected, and has shown a significant Life span-extending effect, in particular in the treatment of testicular tumor, bladder cancer, ureteral tumor and ovarian cancer. While CDDP has excellent antitumor activity, it produces serious toxicity and, above all, its nephrotoxicity is considered as a dose-regulating factor. In order to alleviate such toxicity, such measures as the simultaneous use of diuretics upon administration of CDDP and hydration have been taken, although the toxicity-alleviating effects of these measures are not satisfactory in some patients. In particular where CDDP is repeatedly administered, its accumulated toxicity tends to grow to a point where in certain patients with manifested nephrotoxicity its dose is obliged to be reduced or the drug has to be replaced, with the result that the otherwise possible life span extension is lost. The nephrotoxicity is a serious problem in other therapies as well, for example, in the treatment of ovarian cancer wherein the dose of CDDP is increased, while making administration intervals as short as possible, to enhance the dose intensity. In order to overcome such problems, many attempts to search for compounds capable of alleviating CDDP's nephrotoxicity have been made. Thus, for example, such compounds as sodium thiosulfate, acetazolamide, selenium dioxide, sodium selenate, cysteine, 3-aminobenzamide, phosphomycin and bismuth subnitrate have been reported to show nephrotoxicity-alleviating activity, although these compounds have yet to be put into practical use clinically. Furthermore recent years have seen extensive developments of drugs possessing nephrotoxicity-alleviating activity, as demonstrated, for example, by the recent approval of glutathione in Italy, application for approval of amifostin in the United States of America and clinical investigation of ulinastin now going on in Japan.

On the other hand, it is also known that when CDDP is administered in combination with the above mentioned toxicity alleviator or the like for the suppression of side effects like nephrotoxicity, the antitumor activity of CDDP itself is suppressed. Accordingly, it has been a technical problem in this field to achieve the desired effects without lowering the antitumor activity.

Objects of Invention

The objects of the present invention are to provide a pharmaceutical composition for use as a drug to alleviate the nephrotoxicity caused by a drug administered to the living organism, which composition contains S-adenosyl-L-methionine (hereinafter referred to as SAMe), and also to provide a pharmaceutical composition for use as an antitumor activity potentiator capable of potentiating the antitumor activity of platinum complex compounds, which composition contains SAMe as an active ingredient.

Disclosure of Invention

In order to achieve the above described objects, the present inventors have made extensive studies on SAMe, focusing attention on the fact that glutathione or the like SH-compounds produced in the living organisms detoxicate active oxygen or chemically reactive toxicants through reaction therewith. As a result, the afore-mentioned objects have now been found to be achievable in accordance with the present invention.

SAMe is known to be a compound which exists in the cells of every living organism and which is involved in many important reactions in the living organisms. SAMe, however, is a very unstable compound and hence it was difficult to obtain it in sufficiently large quantities and in sufficiently pure form to render the investigation of its pharmacological effects possible. In recent years (the 1980's) it became possible to obtain SAMe as its stable salts, and studies on different pharmacological actions and biochemical behavior have come to be easily made. As a result of screening these stable salts of SAMe for different pharmacological effects, positive effects on hepatic disturbances, depression, and osteoarthropathy (Japanese published examined patent application No. 56-10920 (JP, B, 56-10920)), on acute brain disturbances (Japanese published examined patent application No. 2-7293 (JP, B, 2-7293)) and on Parkinson's disease or AIDS-associated immunodeficiency, as well as cytotoxicity on certain cancer cells, have been reported, and in Italy, Germany etc. they have been put into clinical use as pharmaceuticals against hepatic disturbances, depression and osteoarthropathy.

The present inventors made studies, in an attempt to find further new pharmacological effects of SAMe, on the post-administration absorption, distribution, metabolism and excretion of SAMe, and found surprisingly that SAMe, when administered intravenously, concentrates specifically at the renal tissue, where it is converted through the process of transmethylation to S-adenosylhomocysteine (hereinafter referred to as SAH) which in turn is converted to such compounds as homocysteine, cysteine and glutathione. It was also noted that there was no increase in the blood level of these SH-compounds after the SAMe administration.

After further extensive studies thereon, the present inventors have found that SAMe possesses such an effect as to ameliorate those damages in the renal tissue caused by antibiotics such as cephaloridine, or immunosuppresants such as cyclosporin.

Furthermore, the present inventors have found that SAMe possesses a significant potentiation effect on the antitumor activity of CDDP against certain tumor species, far from weakening the antitumor activity of CDDP.

Thus, in accordance with the present invention there is provided a nephrotoxicity alleviator for alleviating the nephrotoxicity caused by a drug administered to the living organism, which is characterized by containing S-adenosyl-L-methionine or a salt thereof as an active ingredient, as well as such a nephrotoxicity alleviator as described above wherein the drug administered to the living organism is cisplatin.

SAMe is known to be an extremely safe compound with the $LD_{50}$ value (intraperitoneal administration) being 2,000–2,500 mg/kg in accordance with acute toxicity tests in the rat.

SAMes are known compounds and may be prepared by any known conventional means.

Because of the sulfonium cation being present in the molecule, SAMe exists always in the form of salts with anions and because of the amino groups and the basic nitrogen atoms being contained in the molecule, simultaneously in the form of varied salts formed with respect to such groups and/or atoms.

Accordingly, the drug of the present invention may be normally in the form of SAMe as such or in the form of a composition containing SAMe as an active ingredient.

Examples of stable salts of SAMe usable in the drug of the present invention include those with sulfuric acid, hydrochloric acid, p-toluenesulfonic acid, methanesulfonic acid, ethanesulfonic acid, chondroitin sulfate or disulfonic acid of the general formula $HO_3S(CH_2)mSO_3H$, wherein m is 2–12, as well as double salts consisting of one or more of them.

Examples of the disulfonic acids described above include 1,2-ethanedisulfonic acid, 1,3-propanedisulfonic acid, 1,4-butanedisulfonic acid, 1,5-pentanedisulfonic acid, 1,6-hexanedisulfonic acid, 1,8-octanedisulfonic acid and 1,10-decanedisulfonic acid.

A specific example of the double salts described above is adenosyl-L-methionine tosylate sulfate wherein the SAMe/sulfuric acid/p-toluenesulfonic acid molar ratio is 1:2:1.

Examples of the platinum complex compounds described above include cisplatin (cis-diamine-dichloro-platinum; CDDP), carboplatin, dichloro-ethylenediamine-platinum (II), 1,2-diamino-cyclohexyl-platinum (II)-malonate or sulfate, diisopropylamino-trans-dihydroxy-cis-dichloro-platinum (IV), (–)-(R)-2-aminomethylpyrrolidine (1,1-cyclobutanedicarboxylate)platinum (II)-monohydrate and cis-diamineglycolateplatinum.

In the antitumor activity potentiator of the present invention, one or more of these platinum complex compounds may be incorporated into the drug. The dose of platinum complex compound is dependent on the type of the antitumor agent and hence by no means specified, although it is normally preferred to be 0.5–50 mg/kg per day when estimated from clinical doses used in practice as well as basic pharmacological experiments.

The platinum complex compound(s) as antitumor agent may be incorporated into the nephrotoxicity alleviator or antitumor activity potentiator of the present invention. In these cases, the ratio of the platinum complex compound(s) to the SAMes used will vary depending upon the type of the platinum complex compound(s) and also upon that of the SAMes. It is generally preferred to use 0.02–150, preferably, 10–100 moles of the latter per mole of the former.

The amount of SAMe used will vary depending upon the type of the SAMe and also upon the route of administration. Thus, for example, the amount is preferably in the range of 100–2,000 mg/day as expressed in terms of amount of SAMe where the SAMe/sulfuric acid/p-toluenesulfonic acid molar ratio in the SAMe salt used is 1:2:1.

In the application of the drug according to the present invention, different dosage unit forms prepared from the SAMe by any conventional method and a platinum complex compound-containing antitumor agent prepared in different dosage unit forms may be used simultaneously, separately or consecutively. For these purposes, they may be combined into appropriate formulations. Platinum complex compound may be administered after SAMe has been administered, or conversely SAMe may be administered after platinum complex compound has been administered. Thus the order of their administration is not restricted in any particular way.

In the administration of the drug of the present invention, any suitable dosage form for the particular purpose of the treatment may be used. As oral preparations may be mentioned, for example, tablets, capsular preparations, granules, granula subtilae, powder and enteric preparations. As parenteral preparations may be mentioned, for example, injectable preparations and suppositories. All dosage forms as described above may be prepared in any conventional manner.

For example, to prepare drugs for injection in the form of pulverulent preparations, aqueous solutions are prepared using appropriate water-soluble excipients, e.g. one or more of mannitol, sucrose, lactose, maltose, glucose and fructose, dispensed into vials or ampoules and then freeze-dried, and the vials or ampoules are sealed.

In using the pulverulent preparations for injection as mentioned above, they are generally adjusted to a pH in the vicinity of 7 by using any bases of different kinds, for example, potassium hydroxide or sodium hydroxide or their corresponding bicarbonate or carbonate.

As oral preparations may be mentioned, for example, tablets, capsular preparations, granules, granula subtilae, powder and enteric preparations.

To prepare enteric preparations, excipients (e.g. mannitol, sucrose, lactose, maltose, starches or calcium phosphate), lubricants (e.g. magnesium stearate), binders (e.g. carboxymethyl cellulose, methyl cellulose, gelatine or gum arabic), disintegrators (e.g. calcium carboxymethyl cellulose) etc. are chosen as appropriate to prepare such dosage forms as tablets, granules or granula subtilae, which are then coated with one or more of enteric base materials such as cellulose acetate phthalate, hydroxypropyl methyl cellulose phthalate, polyvinylalcohol phthalate, styrene/maleic acid copolymers, styrene/maleic anhydride copolymers, methyl acrylate/methacrylic acid copolymers or methyl methacrylate/methacrylic acid copolymers.

Furthermore, enteric granules or granula subtilae may be filled into capsules to give capsular preparations.

Enteric capsular preparations may be prepared by coating capsular preparations with enteric base materials or using capsules manufactured by the use of enteric base materials alone or mixed with gelatine.

Examples of suppositories are those prepared by the molding of homogeneous mixtures of heat-melted lipophilic and hydrophilic bases. The lipophilic bases may be, for example, such suppository bases (semi-synthetic glycerides) prepared by mixing cacao fatty acid triglyceride with fatty acid monoglyceride and/or fatty acid diglyceride in different proportions, and the hydrophilic bases may be, for example, polyethylene glycol or glycerogelatine.

In the following will now be given some examples of pharmaceutical preparations in accordance with the present invention.

EXAMPLES

Example 1

Distilled water for injection use was used to prepare a total volume of 3,000 ml of an aqueous solution of 384 g of a SAMe double salt with the SAMe/sulfuric acid/p-toluenesulfonic acid molar ratio being 1:2:1 and 240 g of mannitol. The solution was sterilized by filtration through a Millipore filter (0.22 micron), dispensed in 1.5 ml portions into vials with a capacity of 5 ml and freeze-dried, whereafter the vials were immediately sealed tightly with a stopper to afford pulverulent preparations for injection.

Example 2

Distilled water for injection use was added to 936 g of powder containing 576 g of the same SAMe double salt as in Example 1 and 360 g of mannitol to prepare a total volume of 2,250 ml of aqueous solution. The solution was sterilized by filtration through a Millipore filter (0.22 micron), dispensed in 4.5 ml portions into vials with a capacity of 15 ml and freeze-dried, whereafter the vials were immediately sealed tightly with a stopper to prepare pulverulent preparations for injection.

Example 3

Granules were prepared in the conventional manner from a homogeneous mixture of 576 g of the same SAMe double salt as in Example 1, 114 g of mannitol, 150 g of corn starch and 10 g of magnesium stearate. Separately, 108 g of hydroxypropyl methyl cellulose phthalate, 28 g of shellac and 14 g of glycerin fatty acid ester were dispersed in a mixture of 462 g of methylene chloride, 922 g of isopropyl alcohol and 462 g of water. This dispersion was used to coat the previously prepared granules, and the resulting coated product was filled in 500 mg portions into capsules to give capsular preparations.

Example 4

To 1,424 g of a suppository base containing fatty acid triglyceride as the major component was added 576 g of the same SAMe double salt as in Example 1 to give a homogeneous dispersion, from which suppositories each weighing 2.0 g were prepared.

In the following will now be illustrated the side effects-alleviating and/or antitumor activity-potentiating effects obtained by the combined use of the drug of the present invention with platinum complex compounds.

In the examples below, a liquid preparation for injection of cisplatin (Briplatin® for injection, manufactured by Bristol-Myers) was used as CDDP and the pulverulent preparation for injection prepared in Example 1 which upon reconstitution had been adjusted to a pH of 7 using 4N sodium hydroxide was used as SAMe.

The intravenous administration of the drug according to the invention has been demonstrated by the following experiments to accumulate the SAMe specifically in the renal tissue, and also to produce no increase in the blood (plasma) level of such SH compounds as homocysteine, cysteine and glutathione. Test method: To 6-week-old rats of the SD strain was intravenously administered SAMe in physiological saline (30 mg/kg, pH 6), and the blood level of SH group-containing compounds in the renal tissue was measured thereafter at 30, 60 and 120 minutes (N. Kaplowits et al., J. Pharmacol. Exp. Ther., 1977, 200, 279–286).

The test results are shown in the table below.

TABLE 1

| | Post-administration concentration of SH compounds in blood plasma or renal tissue Concentration (as converted to glutathione concentration) ± S.D. | | | |
| --- | --- | --- | --- | --- |
| | 0 min. | 30 min. | 60 min. | 120 min. |
| Renal[1] tissue | 1029.1 ± 58.6 | 1219.3 ± 68.3* | 1256.0 ± 125.3* | 1201.1 ± 37.8* |
| Blood[2] plasma | 14.2 ± 3.2 | 12.2 ± 2.7 | 12.5 ± 2.1 | 18.5 ± 3.0 |

[1] μg/g organ
[2] μg/ml blood plasma
*p < 0.05 (compared to values prior to SAMe administration)

The values in the table for the concentration of SH compounds in the renal tissue and blood plasma presented as means ± standard deviation as calculated on the assumption that all the SH compounds were glutathione.

Reference will now be made to tests conducted to determine the alleviatory effect of SAMe on the nephrotoxicity caused by CDDP.

Test Example 1

(Alleviatory effect of SAMe on the nephrotoxicity caused by CDDP)

Mice of the CDF1 strain (male, with a weight of 25.0–27.6 g) were divided into four groups of four animals each. The animals of the first and second groups were each administered intraperioneally with CDDP and the SAMe double salt as obtained in Example 1 above in the doses indicated in Table 2. (Hereinafter SAMe doses will be expressed in terms of the SAMe content in the SAMe double salt used.) Blood samples were taken on day 6 to measure the level of blood urea nitrogen (BUN) and creatinine. For the purpose of comparison, the third group was administered with CDDP alone and the fourth group, as control group, was administered with physiological saline alone. The results are shown in the table below.

TABLE 2

| Group No. | Test drug | Dose (mg/kg) | Creatinine concentration (mg/dl) | BUN concentration (mg/dl) |
| --- | --- | --- | --- | --- |
| 1 | CDDP SAMe | 12 100 | 0.33 ± 0.05 | 25.8 ± 7.2 |
| 2 | CDDP SAMe | 12 30 | 0.43 ± 0.17 | 34.2 ± 9.6 |
| 3 | CDDP | 12 | 0.70 ± 0.08 | 54.0 ± 16.7 |
| 4 | Control | — | 0.25 ± 0.10 | 17.0 ± 0.67 |

The values for the creatinine concentration and BUN concentration are presented as means ± standard deviation.

As clearly seen from the test results shown above, the drug of the present invention, when administered together with CDDP, suppressed dose-dependently the increase in the level of BUN and creatinine, demonstrating a significant alleviation of nephrotoxicity.

Test Example 2

(Effect of SAMe on the nephrotoxicity (BUN) after the single administration of CDDP in the dog)

Nine beagle dogs (weighing 10.2–14.5 kg; 24–36 months of age) were divided into three groups of three animals each. The first group was administered intravenously with 4 mg/8 ml/kg of CDDP, and the second and third groups were administered intravenously with 30 mg/kg and 100 mg/kg (as the SAMe content) of the SAMe salt obtained in Example 1 (hereinafter referred to simply as the SAMe salt), respectively. (The SAMe salt was adjusted upon reconstitution to a pH of 5 and its intravenous administration was performed immediately prior to the CDDP administration.) The control group received CDDP and physiological saline. BUN values were measured every two days after the administration and compared.

The results are shown in the table below.

TABLE 3

Effect of SAMe on the nephrotoxicity (BUN) after the single administration of CDDP (4 mg/kg) in the dog

| Administration | BUN concentration (mg/dl) on day | | |
|---|---|---|---|
| | 1 | 6 | 12 |
| Physiological saline | 18.4 ± 4.37 | 147.9 ± 35.87 | — |
| SAMe 30 mg/kg | 15.0 ± 1.04 | 167.2 ± 102.30 | 41.62 ± 0.00 |
| SAMe 100 mg/kg | 13.4 ± 2.80 | 27.6 ± 19.151 | 25.5 ± 13.36 |

The values in the table for the BUN concentration are presented as means ± standard deviation.

All the animals of the control group died by day 7 and two out of the three animals of the SAMe (30 mg/kg) administered group died by day 7, whereas all the animals of the SAMe (100 mg/kg) administered group survived.

Test Example 3

(Effect of SAMe on the nephrotoxicity (BUN) after the multiple administration of CDDP in the dog)

Twelve beagle dogs (weighing 8.3–9.2 kg; 8–9 months of age) were divided into four groups.

The first group received three times (i.e. on days 1, 11 and 21) the intravenous administration of 2 mg/4 ml/kg of CDDP and physiological saline and served as the control group.

The second group was intravenously administered three times (i.e. on days 1, 11 and 21) with 2 mg/4 ml/kg of CDDP and 25 mg/kg of the SAMe salt. The SAMe salt was adjusted upon reconstitution to a pH of 5 and its intravenous administration was performed immediately prior to the CDDP administration.

The third group was intravenously administered three times (i.e. on days 1, 11 and 21) with 2 mg/4 ml/kg of CDDP and 50 mg/kg (as SAMe) of the SAMe salt. The SAMe salt was adjusted upon reconstitution to a pH of 5 and the intravenous administration thereof was performed immediately prior to the CDDP administration. The fourth group was intravenously administered three times (i.e. on days 1, 11 and 21) with 2 mg/4 ml/kg of CDDP and 100 mg/kg (as SAMe) of the SAMe salt. The SAMe salt was adjusted upon reconstitution to a pH of 5 and the intravenous administration thereof was carried out immediately prior to the CDDP administration.

BUN values were measured every two days after each of the days of administration (i.e. days 1, 11 and 21).

The thus obtained BUN values were expressed in the corresponding relative values to the first day (day 1) BUN values taken as 100. The results for days 3, 13 and 23 are shown in the table below.

TABLE 4

Effect of SAMe on the nephrotoxicity (BUN) after the multiple administration of CDDP (2 mg/kg) in the dog

| Group No. | Administration | BUN[1] on day | | |
|---|---|---|---|---|
| | | 3 | 13 | 23 |
| 1 | Physiological saline | 117.9 ± 10.92 | 140.1 ± 34.35 | 160.9 ± 13.14 |
| 2 | SAMe 25 mg/kg | 101.9 ± 22.99 | 115.8 ± 26.88 | 124.6 ± 22.94 |
| 3 | SAMe 50 mg/kg | 101.2 ± 4.00 | 110.8 ± 20.86 | 119.2 ± 20.33* |
| 4 | SAMe 100 mg/kg | 102.4 ± 17.98 | 104.4 ± 23.21 | 104.5 ± 16.25** |

[1]The BUN values in the table above are presented as means ± standard deviation relative to the day 1 BUN values taken as 100.
*p < 0.05;
**p < 0.01

The BUN values significantly decreased with increasing doses of SAMe used.

Test Example 4

(Effect of SAMe on the nephrotoxicity (BUN and CRE) following the single administration of CDDP in the rat)

Rats weighing about 180 g were divided into three groups. The first group was administered once with 5 mg/10 ml/kg of CDDP and the second group once with 5 mg/10 ml/kg of CDDP and 10 mg/kg (as SAMe) of the SAMe salt. (The SAMe salt was adjusted upon reconstitution to a pH of 5 and its intravenous administration was performed immediately prior to the CDDP administration.) The control group was administered with physiological saline instead of the SAMe salt. BUN and creatinine (CRE) values were measured on day 7 after administration. The results are shown in the table below.

TABLE 5

Effect of SAMe on the nephrotoxicity (BUN and CRE) following the single administration of CDDP in the rat

| CDDP (mg/kg) | SAMe salt (mg/kg) | Number of animals | BUN concentration (mg/dl) | CRE concentration (mg/dl) |
|---|---|---|---|---|
| — | — | 3 | 19.0 ± 3.6 | 0.53 ± 0.06 |
| 5 | — | 6 | 83.0 ± 42.5 | 1.12 ± 0.50 |
| 5 | 10 | 6 | 22.2 ± 1.9* | 0.57 ± 0.08* |

*: $P < 0.05$ (compared to CDDP- and physiological saline-administered groups)

The values for the BUN and the CRE concentration are presented as means ± standard deviation.

Test Example 5

(Effect of SAMe on the nephrotoxicity (BUN) following the multiple administration of CDDP in the rat)

Rats weighing about 180 g were divided into three groups. The first group was administered three times at five-day intervals with 3 mg/10 ml/kg of CDDP and the second group three times at five-day intervals with 3 mg/5 ml/kg of CDDP and 10 mg/kg (as SAMe) of the SAMe salt. (The SAMe salt was adjusted upon reconstitution to a pH of 5 and its intravenous administration was performed immediately prior to the CDDP administration.) The control group was administered with physiological saline instead of the SAMe salt. BUN values were measured on some days after administration. The results are shown in Table 6.

TABLE 6

Effect of SAMe on the nephrotoxicity (BUN) following the multiple application of CDDP in the rat

| CDDP (mg/kg) | SAMe salt (mg/kg) | BUN concentration (mg/dl) on day 2 | 3 | 6 | 7 | 10 | 11 |
|---|---|---|---|---|---|---|---|
| 3 | — | 21.3 ± 5.5 | 28.4 ± 2.9 | 45.3 ± 16.2 | 29.5 ± 11.2 | 34.0 ± 7.5 | 34.1 ± 8.9 |
| 3 | 10 | 17.3 ± 2.3 | 25.0 ± 2.5 | 18.9 ± 3.2* | 17.1 ± 3.2 | 23.4 ± 1.8* | 19.0 ± 2.4* |

*: $P < 0.05$ (compared to CDDP- and physiological saline-administered groups)

The values for the BUN concentration in the table are presented as mean ± standard deviation.

Test Example 6

(Effect of SAMe on the nephrotoxicity (BUN) following the multiple application of CDDP in the mouse)

Mice weighing about 24–28 g were divided into three groups. The first, second and third groups were administered, twice at a five-day interval in each case, with 8 mg/8 ml/kg of CDDP; 8 mg/8 ml/kg of CDDP and 30 mg/kg (as SAMe) of the SAMe salt; and 8 mg/8 ml/kg of CDDP and 90 mg/kg (as SAMe) of the SAMe salt, respectively. (The SAMe salt was adjusted upon reconstitution to a pH of 5, and its intravenous administration was performed three times per day, i.e. at the time of, and 30 and 60 minutes after, the CDDP administration, at a dose of 10 mg/kg or 30 mg/kg each time. ) The control group was administered with physiological saline. BUN values were measured on some days after administration.

The results are shown in the table below.

TABLE 7

| CDDP (mg/kg) | SAMe salt (mg/kg) | Number of animals | BUN concentration (mg/dl) on day 3 | 4 | 7 | 8 |
|---|---|---|---|---|---|---|
| — | — | 4 | 39.6 ± 5.3 | 39.2 ± 5.0 | 41.4 ± 4.2 | 34.8 ± 1.9 |
| 8 | — | 4 | 36.8 ± 7.9 | 44.4 ± 12.4 | 140.6 ± 47.8 | 196.3 ± 82.2 |
| 8 | 10 × 3[1] | 5 | 36.0 ± 8.8 | 41.6 ± 5.0 | 59.4 ± 27.6* | 60.9 ± 36.5* |
| 8 | 30 × 3[2] | 5 | 31.5 ± 2.2 | 39.3 ± 11.6 | 90.9 ± 47.1 | 99.3 ± 72.8 |

*: $P < 0.05$ (compared to CDDP- and physiological saline-administered groups)
[1] Administered intravenously three times at 30-minute intervals in 10 mg/kg portions
[2] Administered intravenously three times at 30-minute intervals in 30 mg/kg portions The values for the BUN concentration in the table are presented as means ± standard deviation.

Test Example 7

(In vitro potentiation effect of SAMes on the antitumor activity of CDDP)

Mouse L1210 and P388 leukemic cells were adjusted to $10^4$ cells/ml in culture medium RPMI 1640, and the mixture was dispensed in 2 ml portions into culture test tubes (Falcon No. 2054) and cultured at 37° C. for 5 hours in the presence of 5% carbonic acid gas in a carbonic acid gas incubator. CDDP and/or SAMes were (was) then added into each culture test tube and incubation was continued for further one hour. The cultures were centrifuged at 1,600 rpm for 5 minutes and the culture medium was removed with suction. Two ml of RPMI 1640 was added to the residue and the mixture was cultured for 72 hours under the same conditions as described above, whereafter the number of cells in each of the resulting cultures was measured on a Coulter counter (Model ZB).

The results are shown in Table 8.

TABLE 8

In vitro potentiation effect of SAMes on the antitumor activity of CDDP

| No. | Test drug | $IC_{50}$ (μM) |
| --- | --- | --- |
| 1 | CDDP + SAMe[2] | 1.7 |
| 2 | CDDP + SAMe[1] | 6.6 |
| 3 | CDDP | 16.2 |
| 4 | SAMe | >1000 |

[1] The SAMe to CDDP molar ratio was 1:10.
[2] The SAMe to CDDP molar ratio was 1:100.

The antitumor activity as expressed in $IC_{50}$ (CDDP concentration which produces 50% inhibition of the growth of L1210 cells in the absence of CDDP) was 16.2 μM when CDDP was used alone. In contrast to this, the combined use of CDDP with the drug of the present invention obtained in Example 1 in 10-fold and 100-fold molar excess over the CDDP gave the $IC_{50}$ values 6.6 and 1.7 μM, respectively.

On the other hand, when the above described drug of the present invention was used alone, the $IC_{50}$ was >1,000 μM.

Test Example 8

(In vivo potentiation effect of SAMes on the antitumor activity of CDDP)

Groups each containing six 8-week-old male mice of the CDF1 strain, weighing 24–28 g, were used. Mouse L1210 leukemic cells ($10^5$ cells) were transplanted into the abdominal cavity (on day 0). One day (on day 1) and five days (on day 5) thereafter, CDDP and/or the drug obtained as in Example 1 were (was) administered intraperitoneally to each group.

Antitumor effects on L1210 of CDDP alone and in combination with the above mentioned drug were presented as % increase in life span (ILS) calculated in accordance with the following equation:

$$\% \; ILS = (T/C - 1) \times 100$$

wherein T stands for the average number of days of survival in the CDDP-administered groups of animals, and C for that in the non-CDDP-administered group (control group) of animals.

When the animals survived 30 days or more, the number of days of survival was deemed as 30 days for the purpose of calculation.

The administration was carried out intraperitoneally each time (on days 1 and 5). As for the test drug doses (mg/kg) in Table 9, those in No. 1, for example, indicate that CDDP and the SAMe salt were used together in the doses 4 mg and 400 mg (as SAMe), respectively. And the changes in body weight are presented as the difference between the mean body weights on days 1 and 7 (average body weight on day 7—average body weight on day 1) for each group.

The results are shown in the table below.

TABLE 9

In vivo potentiation effect of SAMes on the antitumor activity of CDDP

| No. | Test drug | Dose (mg/kg) | ILS (%) | Animals showing 30 days of survival | Change in body weight (g) |
| --- | --- | --- | --- | --- | --- |
| 1 | CDDP | 4 | | | |
|   | SAMe | 400 | 184 | 2/6 | −2.8 |
| 2 | CDDP | 6 | | | |
|   | SAMe | 400 | 241 | 5/6 | −4.8 |
| 3 | CDDP | 4 | 73 | 0/6 | −2.4 |
| 4 | CDDP | 6 | 121 | 0/6 | −4.5 |

The test results described above demonstrate the significant potentiation effect of the drug of the present invention on the antitumor activity of CDDP. Thus, when CDDP (4 or 6 mg/kg) and the SAMe salt described in Example 1 (400 mg/kg as SAMe) were used together many animals showing 30 days or more of survival emerged. On the other hand, the changes in body weight observed upon the combined use of CDDP and the drug of the present invention were similar to those observed upon the administration of CDDP alone.

Test Example 9

Mouse Colon 26 colon tumor cells were adjusted to $5 \times 10^3$ cells/ml in culture medium HEM and EL, he culture was dispensed in 2 ml portions into culture Petri dishes. The cultures were then cultured at 37° C. under 5% $CO_2$ for 24 hours, whereafter they were cultured for further one hour in the presence of different concentrations of CDDP alone or in combination with SAMe in 10-fold or 100-fold molar excess over the CDDP. The culture medium was removed with suction, and after washing once with cold PBS(−) 2 ml portions of fresh medium were dispensed into the cultures, which were then cultured for further 72 hours. The cells were treated with trypsin, diluted and then counted using a Coulter counter.

The antitumor activity of CDDP was calculated from triplicate data and presented as $IC_{50}$ (Table 10).

Test Example 10

Potentiation effect on the antitumor activity against human tumors

Human tumor cells which are listed below were adjusted to $5 \times 10^3$–$2 \times 10^4$ cells/ml in culture medium RPMI 1640 (N.B. 1) or MEM (N.B. 2), and the respective cultures were dispensed in 2 ml portions into culture Petri dishes. They were cultured for 24 hours at 37° C. under 5% $CO_2$ and then for further one hour in the presence of different concentrations of CDDP alone or in combination with SAMe in 10-fold or 100-fold molar excess over the CDDP. After the culture medium was removed with suction, the respective residues were washed once with cold PBS (−), supplemented with 2 ml portions of fresh medium and then cultured for further 72 hours. The cells were treated with trypsin, diluted and then counted using a Coulter counter. The antitumor activity of CDDP was calculated from triplicate data and presented as $IC_{50}$ (Tables 11 and 12).

N.B. 1:

Culture medium RPMI 1640: 10% fetal calf serum, 20 μM 2-mercaptoethanol, Kanamycin (100 μg/ml)

N.B. 2:

Culture medium MEM: 10% fetal calf serum, Kanamycin (60 μg/ml)

Human tumor cells used:

A549: pulmonary adenocarcinoma;
LU65: pulmonary cancer;
MKN28: gastric adenocarcinoma;
MKN45: gastric adenocarcinoma;
DLD-1: colon adenocarcinoma;
WiDr: colon adenocarcinoma;
PA-1: ovarian teratoma;
MCAS: ovarian cyst adenocarcinoma;
ACHN: renal adenocarcinoma The results are shown in Tables 10, 11 and 12, in which the designations in %he columns for compound stand for the following:

CDDP was used in combination with SAMe in 10-fold molar excess over the CDDP.

CDDP was used in combination with SAMe in 100-fold molar excess over the CDDP.

TABLE 10

| Compound | $IC_{50}$ (μM) | | |
|---|---|---|---|
| | L1210 | P388 | Colon 26 |
| CDDP | 16.2 | 3.5 | 41.7 |
| | (1.0) | (1.0) | (1.0) |
| CDDP + SAMe[1)] | 6.6 | 2.2 | 18.8 |
| | (2.5) | (1.6) | (2.2) |
| CDDP + SAMe[2)] | 1.7 | 0.9 | 14.9 |
| | (9.5) | (4.2) | (2.8) |

The parenthesized values in the table are the rates of potentiation of the antitumor activity of CDDP by the combined use of CDDP with SAMe, which are calculated by the following formula:

($IC_{50}$ for CDDP)/($IC_{50}$ for CDDP+SAMe)

TABLE 11

| Compound | $IC_{50}$ (μM) | | | | |
|---|---|---|---|---|---|
| | A549 | Lu65 | MKN28 | MKN45 | DLD-1 |
| CDDP | 18.7 | 20.3 | 62.8 | 25.4 | 23.5 |
| | (1.0) | (1.0) | (1.0) | (1.0) | (1.0) |
| CDDP + SAMe[1)] | 15.7 | 15.4 | 31.0 | 14.7 | 16.4 |
| | (1.2) | (1.3) | (2.0) | (1.7) | (1.4) |
| CDDP + SAMe[2)] | 16.2 | 9.9 | 42.3 | 15.6 | 18.1 |
| | (1.2) | (2.1) | (1.5) | (1.6) | (1.3) |

TABLE 12

| Compound | $IC_{50}$ (μM) | | | |
|---|---|---|---|---|
| | WiDr | MCAS | PA-1 | ACHN |
| CDDP | 37.7 | 149.9 | 4.1 | 48.4 |
| | (1.0) | (1.0) | (1.0) | (1.0) |
| CDDP + SAMe[1)] | 24.6 | 27.4 | 3.8 | 28.5 |
| | (1.5) | (5.5) | (1.1) | (1.7) |
| CDDP + SAMe[2)] | 17.2 | 31.0 | 3.6 | 16.8 |
| | (2.2) | (4.8) | (1.1) | (2.9) |

As shown in the test results indicated in the tables, the antitumor activity of CDDP in terms of $IC_{50}$ was found to be 3.5–41.7 μM for mouse tumors and 4.1–149.9 μM for human tumors. In the presence of SAMe in 10-fold or 100-fold molar excess over the CDDP, the antitumor activity of CDDP vis-a-vis any off the tumor cells was found to be potentiated by a factor, in terms of $IC_{50}$, of 1.1–9.5. Furthermore, the $IC_{50}$ values fox SAMe alone vis-a-vis the respective tumor cells were all 1,000 μM or more.

Test Example 11

(Potentiation effect of intraperitoneally or intravenously administered SAMes on the antitumor activity against mouse tumors)

Groups each containing six 8- to 9-week-old male CDF1 mice weighing 24–28 g were used. Mouse L1210 leukemic cells ($10^5$ cells) were transplanted into the abdominal cavity (on day 0). On day 1 and on day 5, the administration of CDDP or the simultaneous administration of CDDP and SAMe was performed intraperitoneally or intravenously.

Antitumor effects of CDDP alone and in combination with SAMe were presented as ILS.

TABLE 13

Potentiation effect of SAMes on the antitumor activity of CDDP (intraperitoneal administration)

| Dose (mg/kg) | | | Animals showing |
|---|---|---|---|
| CDDP | SAMe | ILS (%) | 30 days of survival |
| 4 | — | 78 | |
| 4 | 100 | 113 | |
| 4 | 200 | 204 | 3/6 |
| 4 | 400 | 239 | 5/6 |
| 6 | — | 84 | |
| 6 | 100 | 126 | |
| 6 | 200 | 192 | 2/6 |
| 6 | 400 | 201 | 4/6 |

The table shown above demonstrates the significant potentiation effect of SAMe on the antitumor activity of CDDP. Thus, when CDDP (4 or 6 mg/kg) and SAMe (100–400 mg/kg) were intraperitoneally administered simultaneously many animals showing 30 days or more of survival emerged.

TABLE 14

Potentiation effect of SAMes on the antitumor activity of CDDP (intravenous administration)

| Dose (mg/kg) | | |
|---|---|---|
| CDDP | SAMe | ILS (%) |
| 4 | — | 28 |
| 4 | 10 | 36 |
| 4 | 10 × 3[1)] | 38 |
| 4 | 30 | 48 |
| 4 | 30 × 3[1)] | 53 |

[1)]SAMe was administered in the same dose at the time of the administration of CDDP and twice thereafter at 30 minutes intervals.

The simultaneous intravenous administration of CDDP (4 mg/kg) and SAMe (10–90 mg/kg) was found to potentiate, in dependence upon the dose of SAMe administered, the antitumor activity of CDDP alone. Multiple administration of the same dose of SAMe gave a higher potentiation effect on the antitumor activity of CDDP alone.

Potentiation effect on the antitumor activity against human tumors

Groups each containing three to four 6- to 8-week-old female BALB/c nude mice weighing 24–28 g were used and the human tumors listed below ($10^6$–$10^7$ cells) were subcutaneously transplanted. After a predetermined tumor volume (200–300 mm³) was reached (day 1) CDDP was intraperitoneally or intravenously administered either alone or simultaneously together with SAMe (400 mg/kg). The longest and shortest diameters and the height of tumors, designated as a, b and h (mm), respectively, were used to calculate the tumor volume in accordance with the following equation:

$$\text{Tumor volume (mm}^3\text{)} = \tfrac{1}{2} \times a \times b \times h$$

The antitumor activity was determined on the basis of the rate of increase in tumor volume (i.e. the ratio of the tumor volume on day n to that on day 1) for each animal.

The human tumor cells used were, for example,

A549: pulmonary adenocarcinoma;
LU65: pulmonary cancer,
MKN28: gastric adenocarcinoma;
MKN45: gastric adenocarcinoma;
DLD-1: Colon adenocarcinoma;
WiDr: colon adenocarcinoma;
PA-1: ovarian teratoma;
MCAS: ovarian cyst adenocarcinoma; and
ACHN: renal adenocarcinoma Test Example 12

Mice with human pulmonary cancer (Lu 65) were intraperitoneally administered on days 1 and 5 with CDDP (6 mg/kg) and SAMe (400 mg/kg).

As a result, the combined use of CDDP and SAMe produced a potent antitumor effect as compared to the use of CDDP alone, thus giving rise to a strong inhibition on the tumor growth. In groups administered with both CDDP and SAMe, there were some animals which even showed a shrinkage in tumor.

Also against other human cancers tested, the combined use of CDDP and SAMe was found to give an equivalent or more potent inhibitory effect on tumor growth as compared to the use of CDDP alone.

Thus, in accordance with the present invention, the combined administration of platinum complex compound as antitumor agent and the drug of the invention has been found to produce not only significant alleviation of such side effects as observed with the antitumor agent used alone, e.g. nephrotoxicity and neurotoxicity, but also significant potentiation of the antitumor activity of the antitumor agent as demonstrated in the increase in days of survival.

We claim:

1. A method of reducing the nephrotoxicity of cisplatin therapy comprising administering to a patient receiving cisplatin therapy an effective amount of S-adenosyl-L-methionine or a pharmaceutically acceptable salt thereof.

2. The method of claim 1 wherein the amount of S-adenosyl-L-methionine administered is from 100 to 2,000 mg/day.

3. The method of claim 1 wherein the cisplatin and S-adenosyl-L-methionine are administered simultaneously or separately.

4. A method of enhancing the effect of cisplatin therapy against tumors comprising administering to a patient receiving cisplatin therapy an effective amount of S-adenosyl-L-methionine or a pharmaceutically effective salt thereof.

5. The method of claim 4 wherein the amount of S-adenosyl-L-methionine administered is from 100 to 2,000 mg/day.

6. The method of claim 4 wherein the cisplatin and S-adenosyl-L-methionine are administered sinmltaneously or separately.

* * * * *